United States Patent [19]

Fanger et al.

[11] 4,200,792

[45] Apr. 29, 1980

[54] METHOD OF AND APPARATUS FOR ASCERTAINING THE VOLUME COMPONENTS OF A THREE-COMPONENT MIXTURE

[75] Inventors: Hans-Ulrich Fanger, Reinbek; Rudolf Pepelnik, Börnsen; Walfried Michaelis, Bullenhausen, all of Fed. Rep. of Germany

[73] Assignee: Gesellschaft für Kernenergieverwertung in Schiffbau und Schiffahrt mbH, Geesthacht-Tesperhude, Fed. Rep. of Germany

[21] Appl. No.: 798,120

[22] Filed: May 18, 1977

[30] Foreign Application Priority Data

May 19, 1976 [DE] Fed. Rep. of Germany ....... 2622175

[51] Int. Cl.$^2$ ............................................ G01N 23/00
[52] U.S. Cl. ..................................... 250/359; 250/435
[58] Field of Search ........... 250/253, 255, 308, 358 R, 250/358 P, 359, 360, 432, 435

[56] References Cited

U.S. PATENT DOCUMENTS

| | | | |
|---|---|---|---|
| 3,452,192 | 6/1969 | Hanken | 250/358 R |
| 3,840,746 | 10/1974 | Kehler | 250/360 |
| 3,843,887 | 10/1974 | Morrison | 250/358 |

*Primary Examiner*—Davis L. Willis
*Assistant Examiner*—Janice A. Howell
*Attorney, Agent, or Firm*—Becker & Becker Inc.

[57] ABSTRACT

A method of and apparatus for ascertaining the volume components of a three-component mixture, according to which the mixture is radiated simultaneously by two gamma sources of different energy. The passed-through radiation is picked up by a common detector, and the detector signals are spectroscoped alone with regard to the components of the two gamma lines. The spectogram is evaluated with regard to the two transmissions and with regard to the extinction coefficient pairs for each of the three components $(\mu_{k1},\mu_{k2}),(\mu_{s1},\mu_{s2}),(\mu_{w1},\mu_{w2})$ whereupon, with a known length of the transmission distance, the volume parts of the components are calculated as function $$V = f[\mu_{k1},\mu_{k2},\mu_{s1},\mu_{s2},\mu_{w1},\mu_{w2},t_1,t_2,l].$$

7 Claims, 8 Drawing Figures

METHOD OF AND APPARATUS FOR ASCERTAINING THE VOLUME COMPONENTS OF A THREE-COMPONENT MIXTURE

The well-known correlation between density of matter and absorption of medium-energy γ-radiation has widely been used in various applications. For instance, in two-component systems with known chemical compositions, γ-ray absorption has been applied to determine component fractions due to the specific mean density of the mixture. This method, however, cannot directly be extended to triple-component mixtures which are typical of most conveyor flows.

The present invention relates to a method and an apparatus for determining the proportions by volume of a three-component mixture such as manganese-nodules-sediment-sea water by gamma transmission analysis. The extinction of gamma radiation during its passage through matter depends in a complicated manner the energy of the radiation, on the chemical composition of the matter, and its density. With a predetermined gamma energy and known composition of the measured object, therefore, the density of the measured object can be determined to be checked, it is nevertheless possible by a simple transmission measurement and this method has already proved satisfactory in a variety of ways when used in industry.

Difficulties arise, however, when multi-component mixtures are present and have to be analyzed for their proportions. This is particularly so when two or more components do not differ substantially in density as in the case of manganese-nodules-sediment-sea water mixture for example.

In order to soluve this problem, one aspect of the present invention consists in a method of determining the proportions by volume of a three-component mixture, which will overcome the above mentioned drawbacks.

This object and other objects and advantages of the invention will appear more clearly from the following specification in connection with the accompanying drawings, in which.

Figure 7:
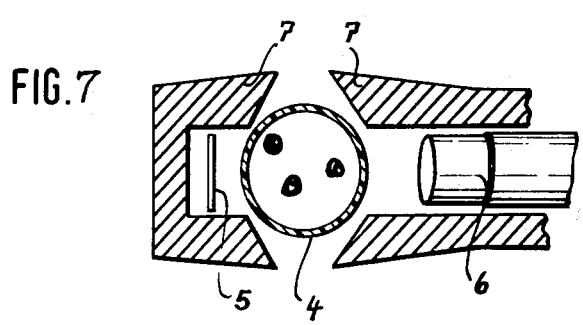
Figure 8:
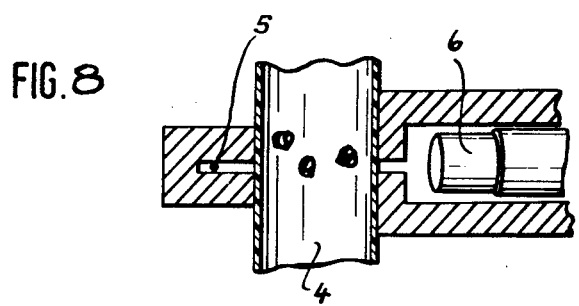

FIGS. 7 and 8 respectively show two diagrammatic sections through a conveying pipe which sections are offset to each other by 90° for a three-component analysis with gamma source and detector.

In order to solve problems, one aspect of to the present invention consists in a method of determining the proportions by volume of a three-component mixture such as manganese-nodules-sediment-sea water by gamma transmission analysis characterized in that the mixture is irradiated simultaneously with two gamma sources of different energy, the transmitted radiation is detected by a common detector and the detector signals are spectroscoped solely with regard to the proportions of the two gamma lines and the spectogram is evaluated with regard to the two transmissions ($t_1$, $t_2$) and with regard to the pairs of extinction coefficients for each of the three components ($\mu_{k1}$, $\mu_{k2}$), ($\mu_{s1}$, $\mu_{s2}$), ($\mu_{w1}$, $\mu_{w2}$) so as then to determine the porportions by volume of the components are ascertained as a function $$V = f[\mu_{k1}, \mu_{k2}, \mu_{s1}, \mu_{s2}, \mu_{w1}, \mu_{w2}, t_1, t_2, l],$$

with a known length (l) of the transmission path, the indices "k", "s" and "w" respectively standing for nodules, sediment and water.

In this case, the gamma energy of the one gamma source should be selected so that the transmission is determined largely by a photoelectric interaction process, which shows a strong dependence on the atomic number of the elements. The transmission measurement with the other gamma source, on the other hand, responds essentially to the density of the measured object. Thus in the example mentioned, the attenuated gamma intensity of the second gamma source determines, above all, the total proportion of the component nodules and sediment, which have similar extinction coefficients but densities which differ noticeably from that of water, while the transmission for the first responds sensitively to the proportion of nodules because the mean atomic numbers of nodules and sediments differ considerably, in contrast to the density.

Both measurements are effected simultaneously with only one detector. The detector signals are spectroscoped only with regard to the proportions of the two gamma lines.

Figure 1:
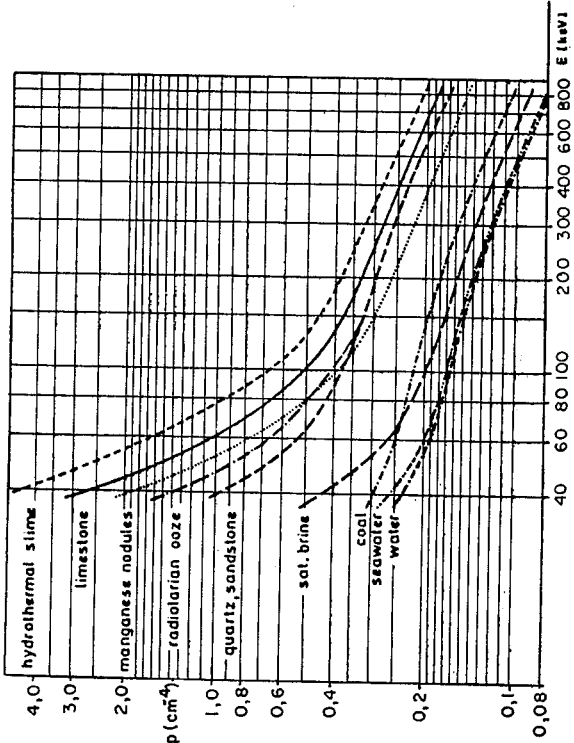
FIG. 1 shows the influence of the chemical Z-number on γ-ray interaction at low energies.
Figure 4:
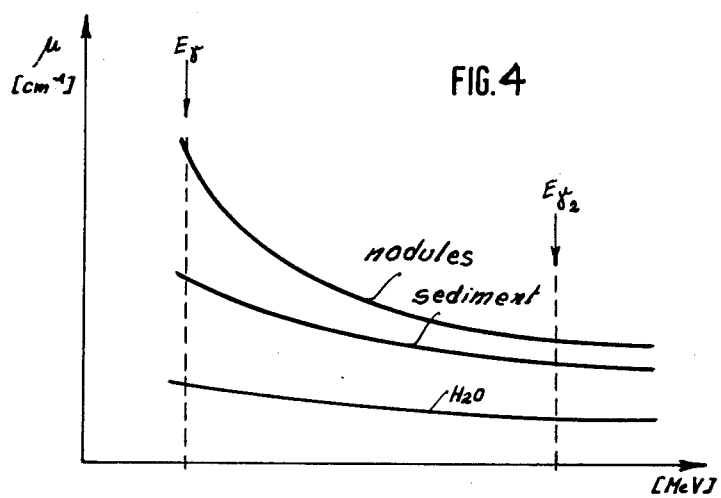
FIG. 4 represents a diagram of the qualitative course of the extinction coefficient in conformity with the energy.

In the case of manganese nodules, for example, the solid-component charge of a collecting and hydraulic lift system consists of marine sediment and nodules which are very similar in specific weight (about 2.0 to 2.4 g cm$^{-3}$) but, fortunately, differ in the chemical Z-number. Since the latter has a strong influence on γ-ray interaction at low energies (FIG. 1), sediment (radiolarian ooze, quartz sand) and nodules may be distinguished by a γ-transmission device using a low-energy beam, while the total solid fraction is determined by absorption of medium γ-rays. More specifically, FIG. 1 shows energy-dependent narrow-beam linear attenuation coefficients for several conveyor-flow components in mining of mineral resources. Typical density values are given at the right-hand side of FIG. 1.

Figure 2:
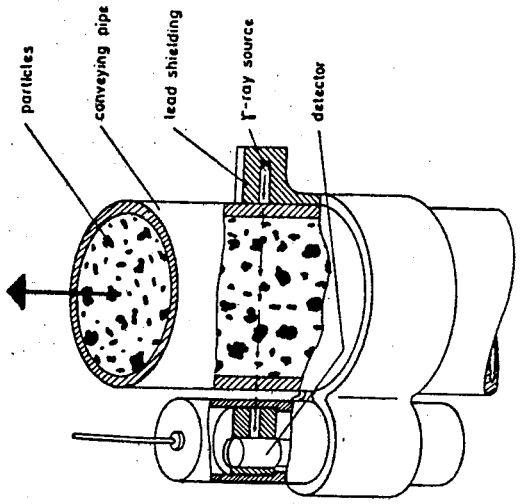
FIG. 2 shows typical pulse-height spectra as obtained from a $^{241}$Am - $^{137}$Cs-source.

Typical pulse-height spectra as obtained from a $^{241}$Am-$^{137}$Cs-source are shown in FIG. 2. The total source strength was approximately 32 mCi. A transmission length of 20 cm was used. The differences in the spectrum shapes arise from different absorber compositions: (i) water, (ii) water+7.5 vol% quartz sand, and (iii) water+8.0 vol.% manganese nodules. FIG. 2 shows experimental transmission spectra with a NaI(Tl) detector. The flow compositions employed are relevant for hydraulic haulage of manganese nodules.

Figure 3:
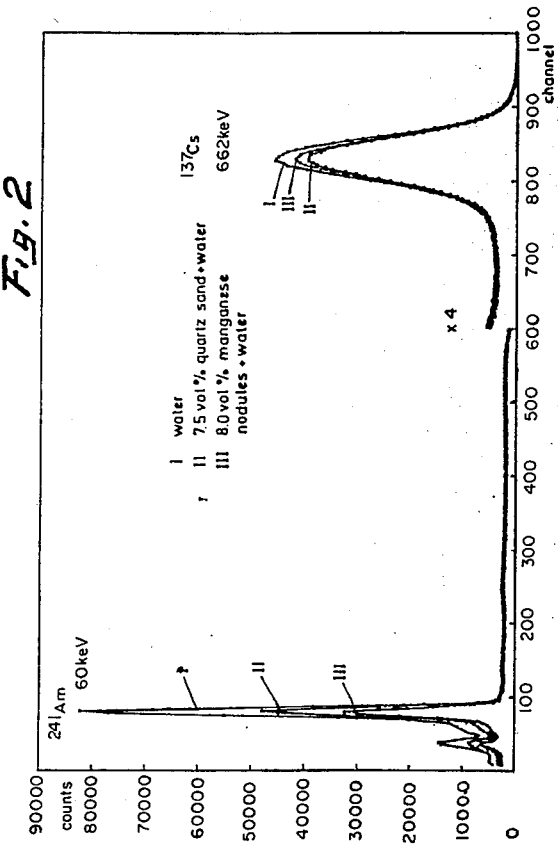
FIG. 3 illustrates a schematic view of a set-up for dual-beam γ-ray transmission analysis.

A schematic view of a set-up for a non-contact dual-beam γ-ray transmission analysis is given in FIG. 3. Source and detector are attached to the conveyor pipe opposite to each other. A line-shaped source is favored for reasons of sensing the largest possible cross section of the tube. In order to minimize interference from Compton processes in the flow, material with scattering angles deviating remarkably from 0°, the γ-radiation is collimated in a plane perpendicular to the pipe axis. Space concentrations determined that way are automatically averaged over a column height defined by flowrate and measuring time.

For determining in a non-contact manner the flow speed in a conveyor pipe, two equivalent γ-ray sources with associated opposite detectors are mounted to the tube at a properly chosen distance, thus forming two transmission gates. Low-energy γ-radiation is strongly absorbed in these gates, for example, by manganese nodules crossing the transmission paths. This absorption induces an instantaneous reduction of the detector output currents. If the distance between the gates is not too long, the patterns in the current fluctuations are identical or at least similar, but time-shifted due to the nodule transit time. The velocity is determined by evaluating the corresponding cross-correlation function.

If the linear extinction coefficients in the three-component mixture water, nodules, and sediment are designated with $\mu_w$, $\mu_k$, and $\mu_s$, then for the attenuated gamma radiation intensity I in relation to the incident radiation $I_o$, there applies the formula:

$$I/I_o = t = \exp[-l(v_k\mu_k + v_s\mu_s + (1 - v_k - v_s)\mu_w)] \quad (1).$$

Following the conventional terminology, t stands for transmission, l designates the total path distance of the collimated beam in the medium to be examined, and v stands for the proportion by volume of nodules and sediment respectively.

Because of the energy dependence of the extinction coefficient $\mu$ or energy, when a gamma radiation is used with lines at the energy $E_1$ and $E_2$, two different transmission values $t_1$ and $t_2$ are obtained which correspond to the coefficients $\mu_{w1}$, $\mu_{k1}$, $\mu_{s1}$, and $\mu_{w2}$, $\mu_{k2}$, $\mu_{s2}$. The solving of the two transmission equations of the type of the equation (1) produces clear values for the proportions by volume $v_k$ and $v_s$ sought according to the equation $$v_k = \frac{(\ln t_1/l + \mu_{w1})(\mu_{w2} - \mu_{s2}) - (\ln t_2/l + \mu_{w2})(\mu_{w1} - \mu_{s1})}{(\mu_{w1} - \mu_{k1})(\mu_{w2} - \mu_{s2}) - (\mu_{w2} - \mu_{k2})(\mu_{w1} - \mu_{s1})} \quad (2)$$

and similarly for $v_s$.

The sensitivity with which the proportions can be determined depends very much on the coefficients, that is to say on the gamma energies selected, and, less critically, on the accuracy with which the statistical quantity "transmission" can for instance be measured for example in percentages.

It is found that the accuracy in the determination of the volume proportion by ($\delta v$) depends not on the magnitude of this proportion itself but increases with the length of the transmission path. The uncertainty in the determination of the proportion by volume depends in the following manner on the measured values $t_1$, $t_2$, and the coefficients:

$$\delta v_k = \frac{1^{-1}}{(\mu_{w1} - \mu_{k1})(\mu_{w2} - \mu_{s2}) - (\mu_{w2} - \mu_{k2})(\mu_{w1} - \mu_{s1})} \cdot [(\mu_{w2} - \mu_{s2})^2(\delta t_1/t_1)^2 + (\mu_{w1} - \mu_{s1})^2(\delta t_2/t_2)^2]^{\frac{1}{2}} \quad (3)$$

In a realistic example, it is found by calculation that with a transmission path of l = 30 cm and with the transmission values measured to 1% accuracy, the proportion of nodules can be determined to within 0.3% accuracy and the proportion of sediment can be determined to within about 0.7%.

The accuracy of the transmission measurement depends on the measuring time, the source strength of the gamma radiation, and structure of the spectrum. The presupposed accuracy of 1% can be can be achieved in 100 seconds with a source strength of about 20 mCi (disregarding the spectral structure.

As already mentioned, the two gamma sources may be formed by a single radionuclide provided said nuclide can radiate in the two energy ranges necessary.

The spectrum of a suitable radionuclide is shown in FIG. 3 which is a plot of transmitted intensity against energy for equal path lengths of three different absorbers. The three curves are for respectively, I water; II 5% sediment (in this case sand) with 95% water; and III 4.5% nodules with 95.5% water. It is clear from this graph that, as explained earlier, at energy $E_1$ where the photo-electric interaction id dominant, the attenuation coefficients of nodules and sediment are markedly different. At energy $E_2$ where the density of the absorbing material is the more important factor, the transmission of nodules and sediment are similar but distinct from that of water.

Figure 5:
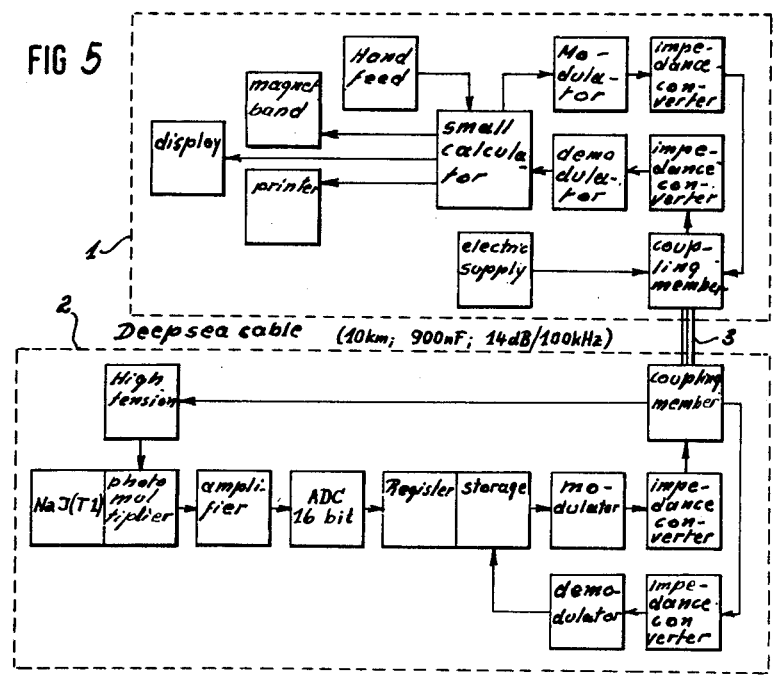
FIG. 5 represents a block diagram showing the various data as to preparation, transmission, processing and delivery.
Figure 6:
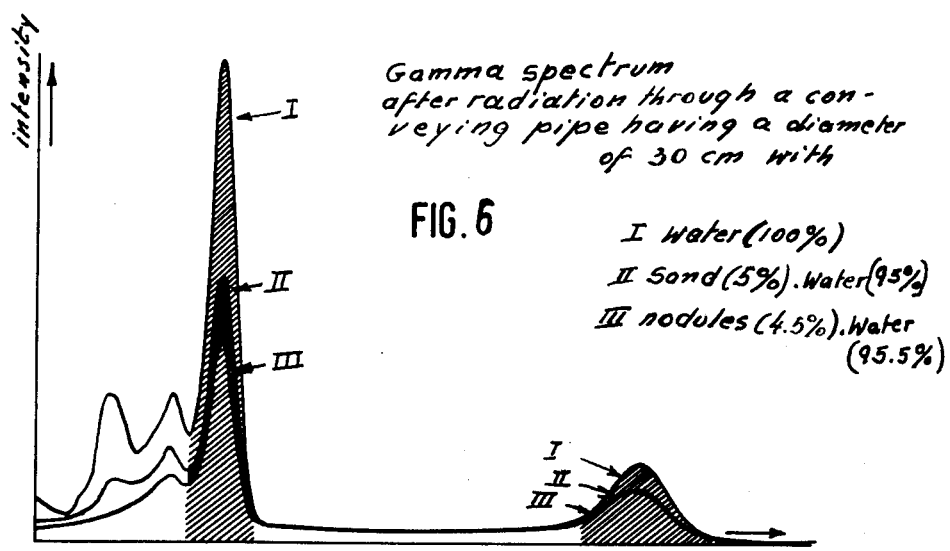
FIG. 6 is a diagrammatic illustration of two gamma spectra in overlap display.

In the exploration of fields of manganese nodules in the deep sea, the method according to the invention may, for example, be carried out as shown in the block diagram of FIG. 5. The components framed by abroken line 1 may be accommodated on board a ship. The components framed by the broken line 2 are in a deep sea probe on a cradle or the like. The two units 1 and 2 are connected to one another via a deep sea cable 3 which with an assumed length of 10 km has a capacity of 900 nF with an attenuation of 14 dB/100 kHz.

The circuitry provided on the ship comprises a minicomputer 10 which supplies an output to a display 11, a magnetic tape deck 12 or a printer 13; and which can receive instructions from a manual input 14. The ship circuitry is connected with the deep-sea cable 3 by means of a coupling network 15, and data from the sea bed can be passed from this network via a matching amplifier 16 and a demodulator 17 to the mini-computer 10. Commands from the mini-computer are passed to the network through modulator 18 and matching amplifier 19. The network 15 is further connected with a power supply 20.

The components housed in the sea bed probe comprise a coupling network 21 which is connected with a high tension unit 22 supplying a photo-multiplier 23. The photo-multiplier signal is amplified at 24 and processed in a sixteen bit analogue-to-digital convertor 25 before being received by a register 26 and store 27. On receipt of commands via the cable 3, network 21, matching amplifier 28 and demodulator 29, the digital signals pass through modulator 30 and matching amplifier 31 to the coupling network 21, and thus to the deep sea cable 3.

Other fields of utilizing the present invention are the ascertainment of volume parts of three-component mixtures, such as manganese nodules-air bubbles-sea water, hydrothermal slimes-NaCl brine-sea water, and coalrocks-water.

FIGS. 7 and 8 show a preferred form of embodiment of the actual probe head. The mixture of components to be examined is conveyed through a conveying tube 4 by appropriate conveying means. At opposite sides of the conveying tube 4, are a line shaped gamma source 5 which radiates in two different energy ranges, and a detector device 6. The probe head is surrounded by collimators 7.

It is, of course, to be understood that the present invention is, by no means, limited to the specific showing in the drawings but also encompasses any modifications within the scope of the appended claims.

What we claim is:

1. A method of determining the proportions by volume of a three-component mixture, in which two components are substantially indistinguishable by gamma ray radiation in density and another component is substantially indistinguishable from one of the other two components by gamma ray radiation in chemical composition, comprising the steps of irradiating a flowing three-component mixture simultaneously with a first and a second gamma source having different energies, lower energy radiation from said first source being selectively absorbed by said two components differing in chemical composition, and radiation from said second source being selectively absorbed by said two components which differ in density, transmitting said radiation a known distance 1, detecting said transmitted radiation by a common detector, analyzing signals from said detector to produce a spectrogram showing solely the proportions of the two gamma energies, then evaluating the spectrogram with regard to the two radiation transmissions ($t_1$, $t_2$) and with regard to the pairs of extinction coefficients for each of the three components ($\mu_{k1}$, $\mu_{k2}$), ($\mu_{s1}$, $\mu_{s2}$), ($\mu_{w1}$, $\mu_{w2}$), and determining the proportions by volume V of the components by calculation as a function f $$V = f(\mu_{k1}, \mu_{k2}, \mu_{s1}, \mu_{s2}, \mu_{w1}, \mu_{w2}, t_1, t_2, l)$$

with a known length (l) of the transmission path where k, s, and w are, respectively, defined as first solid component, second solid component, and liquid.

2. A method according to claim 1, including steps of selecting the first gamma source with regard to its energy, determining the transmission largely by the photoelectric interaction process which shows a strong dependence upon the atomic number of the elements, and also selecting the second gamma source with regard to its energy so that the transmission thereof depends essentially on the density of the measured object.

3. A method according to claim 2, said selecting of energy of the first gamma source is less than 150 KeV and said selecting of the energy of the second source is greater than 300 KeV.

4. A method according to claim 1, wherein there is a step of using radionuclides as Gamma sources.

5. A method according to claim 1, including a step of providing the transmission path selected to be greater than ten times the mean diameter of the manganese nodules.

6. An apparatus for determining the proportions by volume of a three-component mixture, comprising means for irradiating the mixture simultaneously with a first and a second gamma source having different energies, lower energy radiation from said first source being selectively absorbed by said two components differing in chemical composition, and radiation from said second source being selectively absorbed by said two components which differ in density, means for conveying said mixture past said means for irradiating, a common detector means for detecting the radiation transmitted through said mixture, and spectroscopic means for producing a spectrogram solely with regard to the proportions of the two gamma energies, the spectrogram being evaluated with regard to the two radiation transmissions ($t_1$, $t_2$) and with regard to the pairs of extinction coefficients for each of the three components ($\mu_{k1}$, $\mu_{k2}$), ($\mu_{s1}$, $\mu_{s2}$) ($\mu_{w1}$, $\mu_{w2}$) so as to determine the proportions by volume V of the components by calculation as a function f $$V = f(\mu_{k1}, \mu_{k2}, \mu_{s1}, \mu_{s2}, \mu_{w1}, \mu_{w2}, t_1, t_2, l),$$

where k, s, and w are, respectively, defined as first solid component, second solid component, and liquid, and l is the known length of transmission between the means for irradiating and the common detector, a conveying tube having a cross-sectional plane and through which the three-component mixture is conveyed, line-shaped gamma sources and said detector means being arranged diametrically from the means to irradiate the mixture in relation to a common cross-sectional plane of the tube.

7. An apparatus according to claim 6, wherein a measuring device is surrounded by collimators.

* * * * *